(12) United States Patent
Karlsson et al.

(10) Patent No.: US 8,945,824 B2
(45) Date of Patent: Feb. 3, 2015

(54) METHOD OF DETERMINING HYPOXIA

(75) Inventors: Mathias Karlsson, Karlstad (SE); Sofia Hiort af Ornäs, Solna (SE)

(73) Assignee: Calmark Sweden Aktiebolag, Karlstad (SE)

( * ) Notice: Subject to any disclaimer, the term of this patent is extended or adjusted under 35 U.S.C. 154(b) by 0 days.

(21) Appl. No.: 12/101,470

(22) Filed: Apr. 11, 2008

(65) Prior Publication Data

US 2008/0213744 A1 Sep. 4, 2008

Related U.S. Application Data

(63) Continuation-in-part of application No. PCT/SE2007/050738, filed on Oct. 12, 2007.

(30) Foreign Application Priority Data

Oct. 13, 2006 (SE) ..................... 0602158

(51) Int. Cl.
| | | |
|---|---|---|
| *C12Q 1/00* | (2006.01) | |
| *A61B 10/00* | (2006.01) | |
| *A61B 5/00* | (2006.01) | |
| *G01N 33/543* | (2006.01) | |
| *G01N 33/573* | (2006.01) | |
| *A61B 5/15* | (2006.01) | |

(52) U.S. Cl.
CPC ............ *A61B 10/0045* (2013.01); *A61B 5/412* (2013.01); *A61B 10/0048* (2013.01); *G01N 33/54386* (2013.01); *G01N 33/573* (2013.01); *A61B 5/1405* (2013.01); *G01N 2333/904* (2013.01)
USPC .................................. 435/4; 435/26

(58) Field of Classification Search
CPC .......... A61B 17/322; A61B 10/0275
USPC ..................................... 435/4, 26
See application file for complete search history.

(56) References Cited

U.S. PATENT DOCUMENTS

| | | | |
|---|---|---|---|
| 3,783,105 A | 1/1974 | Moyer et al. | |
| 4,803,159 A | 2/1989 | Smith-Lewis | |
| 4,935,346 A | 6/1990 | Phillips et al. | |
| 5,096,669 A | 3/1992 | Lauks et al. | |
| 5,130,231 A * | 7/1992 | Kennedy et al. .................. 435/4 |
| 6,423,011 B1 | 7/2002 | Arulkumaran et al. | |
| 2003/0232396 A1 | 12/2003 | Mathew et al. | |
| 2006/0292663 A1 | 12/2006 | Yaku et al. | |

FOREIGN PATENT DOCUMENTS

| | | |
|---|---|---|
| EP | 1 724 358 A1 | 11/2006 |
| EP | 1 795 127 A2 | 6/2007 |
| FR | 2 511 872 A1 | 3/1983 |
| JP | H-04501768 | 3/1992 |
| JP | 2006-3340 A | 1/2006 |
| RU | 2 144 673 C1 | 1/2000 |
| RU | 2 200 466 C2 | 3/2003 |
| SU | 545335 A1 | 2/1977 |
| SU | 670300 A1 | 6/1979 |
| SU | 1695891 A1 | 12/1991 |
| WO | WO-01/23426 | 4/2001 |
| WO | WO-2004/074815 A2 | 9/2004 |
| WO | WO-2005/034762 | 4/2005 |
| WO | WO 2006/121510 A2 | 11/2006 |
| WO | WO-2008/054303 A2 | 5/2008 |

OTHER PUBLICATIONS

Barkalaya et al. "Biochemical evaluation of bodily influence of high and low temperatures" Abstract only, 1984, Gigiyena Tr. i Prof. Zabolevaniya (Moscow).*
Butter et al. "Effect of glycine in dog and rat liver transplantation", Transplantation, 1993, 56(4):817-822.*
Lackmann et al. "The Predictive Value of Elevation in Specific Serum Enzymes for Subsequent Development of Hypoxic-Ischemic Encephalopathy or Intraventricular Hemorrhage in Full-Term and Premature Asphyxiated Newborns", Neuropediatrics, 1995, 26(4):192-198.*
Mizock et al. "Point-of-care testing of blood Lactate", LaboratoriumsMedizin, 2002, 26(1/2):77-81.*
Kruger et al. "Predictive value of fetal scalp blood lactate concentration and pH as markers of neurologic disability", Am J Obstet Gynecol, 1999, 181:1072-1078.*
Konner "A primer on the av fistula-Achilles' heel, but also cinderella of haemodialysis", Mephrol Dial Transplant, 1999, 14:2094-2098.*
Koukourakis et al. "Lactate dehydrogenase 5 expression in operable colorectal cancer: . . . ", J of Clin. Oncology, 2006, 24(26):4301-4308.*
Office Action for Chinese Application No. 200780037711.4 dated Apr. 25, 2011.
Lindner, W. et al., *Oxygenation and Ventilation in Spontaneously Breathing Very Preterm Infants with Nasopharyngeal CPAP in the Delivery Room*, Acta Paediatr. vol. 91, No. 1 (2007) p. 17-19.
Armitage, N.C. et al., *The Influence of Tumour Cell DNA Abnormalities on Survival in Colorectal Cancer*, Br. J. Surg, vol. 72, No. 10 (1985) pp. 831-834.
Japanese Office Action for Application No. 2011-503943, dated Jul. 31, 2013.

(Continued)

*Primary Examiner* — Bin Shen
(74) *Attorney, Agent, or Firm* — Alston & Bird LLP (57) ABSTRACT

A method of determining hypoxia in fetal scalp blood sampled during labor comprises the determination of total lactate dehydrogenase (LDH) in plasma obtained from the sample. The method can comprise the additional determination of K, Mg, Ca, AST, ALT, lactate in the plasma and/or blood. Increased values of one or more of LDH, Mg, Ca, AST, ALT, lactate are indicative of hypoxia in the fetus. Also disclosed is the use of a plasma separation apparatus in the method.

20 Claims, 7 Drawing Sheets

(56) References Cited

OTHER PUBLICATIONS

"PUBS, FBS Fetal pulse oximetry;" Medical Online; dated 2004.
Mongelli, M., et al,; "Effect of Labour and Delivery on Plasma Hepatic Enzymes in the Newborn;" Journal of Obstet. Gynaecol. Res., vol. 26, No. 1; pp. 61-63; dated 2000.
Pinto, P. V. C., et al.; "Aldolase: I. Colorimetric Determination;" Clin. Chem., vol. 15, No. 5; pp. 339-349; dated May 1969.
Office Action for Japanese Application No. 2009-532327; dated Dec. 26, 2012.
Vitros® DT60 II Chemistry System; Ortho-Clinical Diagnostics, Inc., USA; retrieved on Feb. 4, 2013 from <http://www.orthoclinical.com/en-us/ProductInformation/ClinicalLaboratories/VITROSDT60/Pages/Overview.aspx>.
SYNCHRON CX® System(s): Chemistry Information Sheet; "Lactate Dehydrogenase;" Copyright 2003, Beckman Coulter, Inc; retrieved from <http://anten-service.ru/files/Id-1_442655_476841.pdf>.
Office action for Russian Patent Application No. 2010 140243/10, dated Mar. 26, 2012.
Ilavazhagan, G., et al.; "Effect of vitamin E supplementation on hypoxia-induced oxidative damage in male albino rats"; Aviation Space Environmental Medicine; vol. 72; Issue 10; Oct. 2001; pp. 899-903.
Liu, Y., et al.; "Effects of acute hypoxia on plasma lactic acid and lactic dehydrogenase content in pilots"; Space Medicine & Medical Engineering; vol. 13; Issue 6; Dec. 2000; pp. 414-416.
First Examination Report for India Application No. 2484/CHENP/2009 dated Aug. 29, 2013.
Acosta, S., et al.; "*L-Lactate After Embolization of the Superior Mesenteric Artery*;" Journal of Surgical Research, vol. 143, No. 2; pp. 320-328; dated Dec. 2007; abstract retrieved on Feb. 3, 2014 from <http://www.journalofsurgicalresearch.com/article/S0022-4804(07)00061-3/abstract>.
D'Auria, S., et al.; "*A Protein Biosensor far Lactate*;" Analytical Biochemistry, vol. 283; pp. 83-88; dated 2000; retrieved on Jan. 31, 2014 from <https://www.researchgate.net/publication/12390430_A_protein_biosensor_for_lactate?ev=srch_pub>.
Danse, E. M., et al.; "*Prognosis of Ischemic Colitis: Comparison of Color Doppler Sonography with Early Clinical and Laboratory Findings*;" American Journal of Roentgenology, vol. 175, No. 4; pp. 1151-1154; dated Oct. 2000; retrieved on Feb. 3, 2014 from <http://www.ajronline.org/doi/pdf/10.2214/ajr.175.4.1751151>.
Foster, M., E.; "*Hypovolemia and healing in colonic anastomoses*;" British Journal of Surgery, vol. 72, No. 10; pp. 831-834; dated Oct. 1985.
Karlsson, M., et al.; "*Dynamics of hepatic enzyme activity following birth asphyxia*;" Acta Paediatrica, vol. 95; pp. 1405-1411; dated 2006; abstract retrieved on Jan. 31, 2014 from <http://onlinelibrary.wiley.com/doi/10.1080/08035250600693488/abstract>.
Nordstrom, L.; "*Fetal scalp and cord blood lactate*;" Best Practice & Research Clinical Obstetrics and Gynaecology, vol. 18, No. 3; pp. 467-476; dated Jun. 2004; abstract retrieved on Jan. 31, 2014 from <http://www.bestpracticeobgyn.com/article/S1521-6934(04)00032-X/abstract>.
Sanchez-Nava, J., et al.; "*Increase in glutamic-oxaloacetic and glutamic-pyruvic transaminases and lactic dehydrogenase as a diagnostic aid in perinatal asphyxia*;" Boletin medico del Hospital Infantil de Mexico, vol. 47, No. 6; pp. 372-375; dated Jun. 1990; abstract retrieved on Jan. 31, 2013 from <http://www.ncbi.nlm.nih.gov/pubmed/2222819>.
Saugstad, O. D.; "*Is lactate a reliable indicator of tissue hypoxia in the neonatal period?*" Acta Paediatrica, vol. 91; dated 2002.
Verspyck, E., et al.; "*Fetal Lactic Dehydrogenase Variation in Normal Pregnancy and in Cases on Severe intra-uterine Growth Restriction*;" Prenatal Diagnosis, vol. 19, No. 3; pp. 229-233; dated 1999; abstract retrieved on Jan. 31, 2014 from <http://onlinelibrary.wiley.com/doi/10.1002/(SICI)1097-0223(199903)19:3%3C229::AID-PD511%3E3.0.CO;2-K/abstract>.
International Search Report and Written Opinion for Application No. PCT/SE2007/050738; dated Apr. 4, 2008.
Invitation to Pay Fees for Application No. PCT/SE2007/050738; dated Feb. 1, 2008.
Office Action for Russian Application No. 2010140243/10(057714); dated Nov. 1, 2012.
Hassanein, S. M., et al.; "*Are Serum Lactate Dehydrogenase (LDH), Aspartate Aminotransferase (AST) and Total Creatine Kinase (TCK) Able to Predict Sequel of Perinatal Asphyxia?*" Pediatric Research, vol. 51, Part 2, col. 2675; dated 2002.
Menzel, K., et al.; "*Serum activities of LDH, CPK, GOT, GPT, and LAP in asphyctic newborns*;" Acta Paediactrica Academiae Scientiarum Hungaricae, vol. 15, No. 3-4; pp. 241-254; dated 1974.
International Preliminary Report on Patentability for Application No. PCT/SE2007/050738; dated Apr. 15, 2009.
Office Action for Chinese Application No. 200780037711.4; dated Sep. 23, 2013.
Office Action for European Application No. 09 729 478.9 dated Sep. 17, 2014.
Office Action for Indian Application No. 6461/CHENP/2010 dated Sep. 11, 2014.
Sanders, R. D. et al., *Perinatal neuroprtection*, Current Anaesthesia and Critical Care, vol. 18, No. 4, 215-224 (2007) 1 page.
Vagholkar, K. R., *Healing of Anastomosis in the Gastrointestinal Tract: Retrospective Study of 35 Cases*, Bombay Hospital Journal, vol. 43, No. 2, 269-280 (Apr. 2001) 13 pages.
Supplementary Partial European Search Report for Application No. EP 07 83 5323 dated Nov. 20, 2014.
Lackmann, G. M., *Reference Values for Selected Enzyme Activities in Serum From Healthy Human Neonates*, Clinical Biochemistry, vol. 29, No. 6 (1996) 599-602.

\* cited by examiner

METHOD OF DETERMINING HYPOXIA

CROSS REFERENCE TO RELATED APPLICATIONS

The present application is a continuation-in-part of Application No. PCT/SE2007/050738, filed Oct. 12, 2007, which claims priority to Swedish Application No. 0602158-8, filed Oct. 13, 2006, both of which are hereby incorporated by reference in their entirety.

FIELD OF THE INVENTION

The present invention relates to a method of determining hypoxia. One aspect of the present invention relates to methods of determining hypoxia in fetal scalp blood during labor indicative of a risk of fetal organ dysfunction. In another aspect, the present invention relates to a device for determining hypoxia.

BACKGROUND OF THE INVENTION

Acute perinatal asphyxia, that is, hypoxia (insufficient oxygen saturation of fetal blood) during or close to birth, remains an important cause of neurological damage in form of hypoxic-ischemic encephalopathy (HIE) in newborn infants. It is seen in 2-9/1000 term infants and is followed by cerebral palsy (CP) and death in the severe cases. In a global perspective about 4 million newborn children die each year and about 23% are caused by acute perinatal asphyxia. Due to a lack of resources undeveloped countries are worse off, but as understood by the large numbers also in the western world this is a serious problem. Sweden can be seen as a representative country for the western world wherein asphyxia will occur in about 7/1000 term births leading to 2/1000 children being born with HIE. To prevent persisting damage caused by perinatal asphyxia it is important to detect hypoxia in a fetus as fast as possible upon its onset. Fast detection allows one to make decisions about whether to intervene at a stage where persisting damage has not occurred. The intervention substantially consists in bringing the infant out as quickly as possible by instrumental delivery, in particular by caesarean section.

Detection of acute perinatal asphyxia is presently done by monitoring of fetal heart rate followed by measurement of pH or lactate measurement in fetal scalp blood sampled through the vagina if an ominous fetal heart rate pattern is seen.

pH and lactate are indicators of metabolic acidosis caused by a switch to anaerobic metabolism in situation of insufficient oxygen supply. In an oxygen starved fetus pyruvate is metabolised to lactate and energy. At present measurement of pH is the golden standard. The fast determination of pH however requires about 35 µl of scalp blood, which is not easily obtained. Failure in the first determination is quite common (20%) as some studies indicate. Lactate is easier to measure since only 5 µl of blood is needed and the analysis can be carried out at bed side. Lactate analysis can be carried out within one minute and thus is sufficiently quick.

Lactate and pH are also indicators of acute asphyxia. As such Lactate and pH can provide an indication of a totally healthy fetus subjected to a sudden acute onset of hypoxia-ischemia during birth. A significant proportion of all infants developing hypoxic ischemic encephalopathy have had episodes of hypoxia-ischemia before entering the delivery phase. They are more vulnerable to hypoxia-ischemia during birth and do not respond in the same way as healthy foetuses and therefore the currently used methods are not sufficient for this group of patients.

A method for monitoring childbirth comprising the measurement of lactate in fluids, such as vaginal fluids, is disclosed in WO 2005/034762 A1. Preliminary results from a recent Swedish randomized study of pH and lactate in fetal blood at partum show that lactate, as an indicator of acidosis, is as good as pH. Neither lactate nor pH are ideal predictors of moderate/severe HIE: the sensitivity is only 67% for lactate and 50% for pH, whereas the specificity is about the same, 76% for lactate and 73% for pH. Also, the sensitivity and specificity in predicting acidosis in newborns are less than 70 percent for both lactate and pH. A recent Swedish report concludes that even in fetal monitoring by a combination of cardiotography (CTG) and STAN (analysis of the cardiographic ST segment) there is a risk of not detecting perinatal asphyxia of a kind that may result in encephalopathic damage (SBU Alert-rapport nr 2006-04).

Enzymes known to be elevated in newborn infants subjected to asphyxia during labor are LDH (lactate dehydrogenase), ALT (alanine aminotransferase) and AST (aspartate aminotransferase) also known as liver enzymes. LDH is found in most of the cells in the body, and it is considered an unspecific enzyme. Therefore it is infrequently used in clinical work. Previously LDH was used as a marker of myocardial damage but has now been replaced by more specific tests. AST and, in particular, ALT are more specific to liver damage. In a study on the effect of labor and delivery on plasma hepatic enzymes in the newborn of a group of low-risk Chinese women LDH (lactate dehydrogenase), ALT (alanine transaminase), AST (aspartate transaminase), GGT (γ-glutamyl transaminase) were determined and correlated to maternal and neonatal characteristics (Mongrelli M et al., J Obstet Gynaecol Res, 26(1): 61-63, 2000).

If a fetus is subjected to hypoxia during or close to birth the blood flow in its body will be redistributed from "less important organs" (kidneys, liver, fat and gut) in favor of the brain, heart and adrenals. This tends to damage cells in unprivileged organs. Cell damage results in a leakage of enzymes, which enter circulation. If the hypoxia is severe cells will die, and enzyme concentration increase even more in the blood. The rate of decline of LDH, AST and ALT (between 12-36 hours) makes it possible to detect cases more vulnerable to hypoxia-ischemia during delivery due to previous hypoxia started before the delivery. Hypoxia also affects the balance of electrolytes in the fetal body. One example is the influx of calcium from the blood in to the cells during hypoxia. It is shown that the concentration of serum ionized calcium is increased during hypoxia in a newborn animal model. Calcium also predicts outcome (brain damage or not) in human infants. Other enzymes and electrolytes of interest that are changed during hypoxia in newborn mammals are potassium ($K^+$), magnesium ($Mg^{2+}$), sodium ($Na^+$), glucose, creatinine kinase (CK) and GGT.

In a global perspective about 4 million newborn children die each year and about 23% of these deaths are caused by acute perinatal asphyxia. The pathological mechanism of hypoxia-ischemia leading to injuries of the neurons in the brain is biphasic starting with the primary phase directly after birth. If an infant is successfully resuscitated this primary phase will be followed by a free interval that continues for hours. In two out of seven asphyxiated infants this free interval will be followed by a secondary energy depletion resulting in delayed cell death in the child's brain and a clinical picture with seizures (also known as HIE). The free interval offers a possibility to minimize the delayed cell death by hypothermia treatment (cooling the child's brain to 34.5° C.). Currently, however, there is no reliable means for predicting which child will develop HIE and therefore have benefits from hypothermia treatment.

In addition to during or close to birth, hypoxia is also a serious concern in many other medical conditions. For example, colorectal cancer is one of the most common tumors in both genders, the incidence of which is increasing every year. The current treatment involves a surgical procedure whereby the tumor is removed together with a radical part of the bowel. In the majority of these cases the distal and the proximal ends of the bowel are thereafter put together again. This is referred to as an anastomosis. During this procedure, arterial blood supply to the part of the bowel where the tumor is located is interrupted when the arterial vessels are cut. Post-operative complications due to leakage of the anastomosis can be anticipated in 7-10% of all operations. In such cases, the contents of the bowel will leak out in the abdomen and cause inflammation, peritonitis, sepsis and potentially death. The main reason for this complication is insufficient blood supply to the area for the anastomosis (e.g. hypoxia-ischemia) as a result of the extirpation of the vessels. The current solution is to simply re-operate. Undesirably, it is currently not possible, during surgery, to foresee if the anastomosis will leak or not.

Other areas where hypoxia is a major concern include vascular surgery and liver transplant surgery. For instance, a major factor determining morbidity and mortality in patients after liver transplantation therapy is preservation injury of the hepatic grafts (Leemaster 1997). LDH, AST and ALT leakage into the perfusate is a measure of loss of the membrane integrity of the liver cells (Kebis 2007).

One major shortcoming of prior devices and methods for determining hypoxia is that LDH can only be analyzed in plasma or serum. Further, they require a minimum of 150 microliters of whole blood for such a measurement. Such volume of blood is difficult to receive from small animals, specific tissue or the unborn child during birth. Another problem is that LDH is also present in red blood cells and haemolysis (rupture of red blood cells) will lead to false high values (beyond detection limit).

Thus, there is a need for a method of analyzing LDH, alone or together with electrolytes and liver enzymes, quickly and require only a small amount of blood for detection of hypoxia-ischemia. Additionally, there is a need for improvement in determining the oxygen supply status of a fetus at partum.

BRIEF SUMMARY OF THE INVENTION

The present invention satisfies at least some of the needs by providing a device and method where LDH, and optionally also AST, ALT, Mg, and lactate, can be analyzed within minutes (or alternatively in seconds) in 10 microliters of whole blood. These analyses can be measured together with free haemoglobin to make sure that haemolysis is not present with false increased values of LDH as the result.

Embodiments of the present invention include a method of determining hypoxia, especially hypoxia in fetal scalp blood sampled during labor. In such embodiments, the method can comprise the determination of LDH (lactate dehydrogenase) in plasma. It is preferred to determine, in addition to LDH, one or several markers selected from the group consisting of K, Mg, Ca, AST, ALT, and lactate in said fetal scalp blood. Particularly preferred are the combinations of LDH with any of K, Mg, Ca, AST, ALT, lactate. Also preferred is the combination of LDH, lactate, Mg, and AST and/or ALT.

As used throughout, it should be understood that "LDH" and "lactate dehydrogenase" refer to total lactate dehydrogenase, that is, not to isoenzymes thereof.

In the method of the invention scalp blood, in limited amount (preferably about 5-25 μL) is sampled from a fetus through the vagina during partum in an environment close to the patient. The sample is subjected to separation of plasma (blood serum) from blood cells, in particular from erythrocytes, and the plasma is analyzed for LDH and, optionally, for one or more of K, Mg, Ca, AST, ALT, lactate, to present a result within minutes. As a consequence the medical team may directly conclude if the child suffers from acute asphyxia, i.e. indicating if caesarean section is needed or not. Thanks to the invention a large amount of the suffering related to hypoxia may be eliminated and also a large amount of savings may be achieved.

Figure 1:
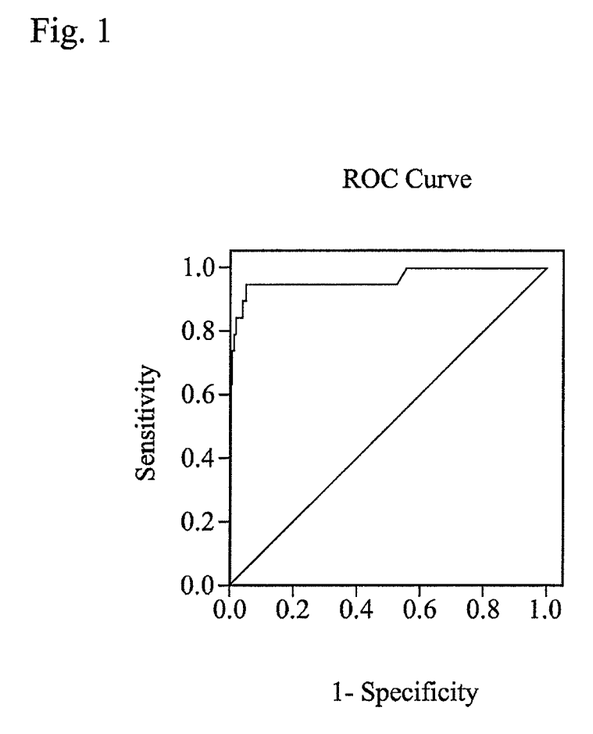
FIG. 1 illustrates a ROC curve for sensitivity and specificity.

In studies performed by the inventor LDH, AST and ALT in blood samples from children were analysed during the first 24 hours. It was found that out of 193 tested children. 19 of these children indicated signs of asphyxia in the form of an Apgar score <7 at the age of five minutes. By means of a ROC curve (see FIG. 1) sensitivity and specificity of 96% for LDH at a cut off value of 1000 U/L could be observed. For HIE the sensitivity is 100% and specificity 96% at the same cut off value. In other words this means that the main marker according to the method of the invention determines 95% (or more) of all children with a true hypoxia correctly at the same time determines 95% of all healthy children as healthy. AST and ALT presented a sensitivity of 86% and a specificity of 90% at a cut off value of 55 U/L and 18 U/L respectively. Despite the fact that this study is preliminary it indicates a surprising improvement compared to existing methods of today.

From a cost perspective the results are astonishing. When using methods of today it is known that it takes about 10 unnecessary caesarean sections to find one child with HIE, i.e. in order to find one HIE-child a total of 11 caesarean sections are done and 10 of these being unnecessary. The sensitivity and specificity of the invention indicates that the outcome would be the opposite, i.e. merely one out of ten caesarean sections would be unnecessary. Accordingly society will save millions and millions and not at least it would result in more children being able to take advantage of a natural birth. Presented below is a table showing the drastic improvements by the method according to the invention compared to known methods.

| Method | LDH | AST/ALT | CTG | pH | lactate |
| --- | --- | --- | --- | --- | --- |
| Sens. HIE | 100% | 90% |  | 46% | 72% |
| Spec. HIE | 96% | 91% |  | 67% | 71% |
| Sens. Apgar | 91% | 86% | 90% | 57% | 66% |
| Spec. Apgar | 92% | 89% | 30% | 71% | 69% |

In healthy persons, erythrocytes are known to contain about 150 times more LDH than serum. Thus it is important to carry out sampling and separation in a manner that does not damage erythrocytes to prevent their LDH content from passing into the plasma. It is also important to take into account the small volumes of scalp blood available for analysis. In the method of the invention a sample of scalp blood is separated into plasma and blood cells by a making the plasma pass through a porous matrix, in this application termed "membrane" on a solid support capable of retaining the blood cells. The plasma is analysed for LDH in a conventional manner. K, Mg, Ca, AST, ALT, and/or lactate can be analyzed in plasma or in blood; if analyzed in blood, the scalp blood sample has to be divided into a portion from which plasma is obtained for the measurement of LDH, and one or more portions for the analysis of the other hypoxia marker(s). It is within the ambit of the invention to use other methods known in the art, such as micro-centrifugation, microfluidic compact disc technology and magnetophoresis, for separating plasma from blood cells in the scalp blood sample of the invention.

Methods for analysis of LDH in fluids such as blood plasma are known in the art and can be adapted to measure LDH in serum obtained from fetal blood; see, for instance, Pinto P V C et al., Clin Chem 15:339-349, 1969. Particular useful is the method disclosed in U.S. Pat. No. 4,803,159, which is herewith incorporated in this application. A commercial apparatus for use in the last mentioned method is on the market (Vitros® DT60 II Chemistry System; Ortho-Clinical Diagnostics, Inc., U.S.A.). Methods for analysis of K, Mg, Ca, ALT, AST, and lactate in blood are routinely used in clinical chemistry and thus within the easy reach of a person skilled in the art.

According to the invention levels of LDH, K, Mg, Ca, ALT, AST, and lactate are elevated in scalp blood sampled from a fetus through the vagina during partum if the fetus is in a hypoxic state, the standard (baseline) being corresponding levels in a fetus during partum and/or immediately after partum in the context of an unproblematic birth. In particular, levels of LDH, ALT and AST are increased by a factor of two, in particular three or more, in a fetus during partum suffering from severe asphyxia, that is, asphyxia which puts the fetus at a higher risk of acquiring HIE.

According to a preferred aspect of the present invention is disclosed a method of determining hypoxia in a sample of scalp blood during labor, comprising providing a point of care device, using at least one, preferably numerous, markers to within minutes determine if acute hypoxia is at hand.

According to a further preferred variation, the device is additionally in communication with analyzing means for one or several of K, Mg, Ca, AST, ALT, lactate.

According to a further preferred aspect is disclosed a plasma separation device for simple and direct use in a device/method of the invention.

In other aspects, the present invention includes a method of assessing hypoxia at a tissue site of a mammal. In such embodiments, the method can comprise the collecting a blood sample from the tissue site, wherein the blood sample comprises plasma and blood cells followed by separating the plasma from the blood cells. The amount of LDH in the plasma is determined and the presence of hypoxia at the tissue site is assessed from the amount of LDH in the plasma. Methods of assessing hypoxia at a tissue site can include analysis of a blood sample from a mammal's gastrointestinal tract (e.g., a mammal's bowel), analysis of a sample from a specific organ (e.g., a mammal's aorta) or cerebrospinal fluid collected for example by microcatheter, analysis of urine or intraperitoneal fluid, and analysis of a sample from an organ to be transplanted into a mammal in need thereof. Methods of assessing hypoxia according to embodiments of the present invention can allow one to predict the likelihood of brain injury after prenatal asphyxia and the assessment of blood circulation to a mammal's limbs before, during, and after a medical or surgical procedure.

The present invention will now be explained in more detail by the description of preferred but not limiting embodiments thereof illustrated in more or less schematic drawings.

BRIEF DESCRIPTION OF THE FIGURES

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides a device and method where LDH, and optionally also AST, ALT, Mg, and lactate, can be analyzed within minutes (or alternatively in seconds) in 10 microliters of whole blood. These analyses can be measured together with free haemoglobin to make sure that haemolysis is not present with false increased values of LDH as the result.

In one aspect, the invention comprises a method of determining hypoxia. According to certain embodiments, the method can comprise collecting a blood sample; and determining the total amount of LDH in the blood. The blood sample can be collected from any mammal or alternatively from any organ to be transplanted into a mammal in need thereof.

In another embodiment, the method of determining hypoxia comprises collecting a blood sample, wherein the blood sample includes plasma and blood cells. Preferably, the plasma is separated from the blood cells such that the plasma can be analyzed without the presence of blood cells. The isolated plasma can be analyzed for the total amount of LDH in the plasma. As such, a determination of LDH can be achieved. Based on the LDH quantity, or alternatively in conjunction with other prognostic markers, a determination of hypoxia can be readily realized.

In one preferred embodiment, the determination of hypoxia includes analyzing a blood sample to determine the quantity or amount of multiple prognostic markers. In one such embodiment, the method comprises determining the amount of LDH in a blood sample, or preferably the plasma thereof, and determining the amount of at least one additional prognostic marker selected from the group consisting essentially of K, Mg, Ca, AST, ALT and lactate.

Preferably, the blood sample for analysis is manipulated such that the plasma is separated from the blood cells. In one embodiment, this separation can be achieved by use of a semi-permeable membrane or centrifuge. When utilizing a semi-permeable membrane, the plasma preferably passes through the membrane and the blood cells are retained on the membrane. Accordingly, the plasma is for all practical purposes isolated from the bulk of the blood cells. The plasma can then be sampled and tested in the absence of blood cells.

According to various embodiments, the sample volume for analysis can be greatly reduced from prior methods. In one embodiment, the volume of blood for determining hypoxia comprises from 5 µL to 60 µL, or from 5 µL to 25 µL, or preferably from about 5 to 15 µL, and in particular 10 µL. In certain embodiments, the volume of blood for determining hypoxia comprises from about 5 µL to 150 µL, or from 10 µL to 120 µL, or from 10 µL to 100 µL, or from 10 µL to 80 µL.

Beneficially, embodiments of the present invention allow for the determination of hypoxia in a wide variety of circumstances. For instance, embodiments of the present invention include, but not limited to, the determination of hypoxia in blood from a fetal scalp, a gastrointestinal tract (e.g., colon anastomosis), specific organs (e.g., liver and aorta), cerebrospinal fluid from a lumbar drain, and organs to be transplanted. Additionally, embodiments of the present invention enable the assessment and/or monitoring of the liver (e.g., in mammal's potentially suffering from multi-organ dysfunction), peripheral tissue (e.g., related to trauma, sepsis, haemorrhage or extensive surgery), prediction of brain injury after prenatal asphyxia, and monitoring of peripheral blood circulation of a mammal.

Figure 2:
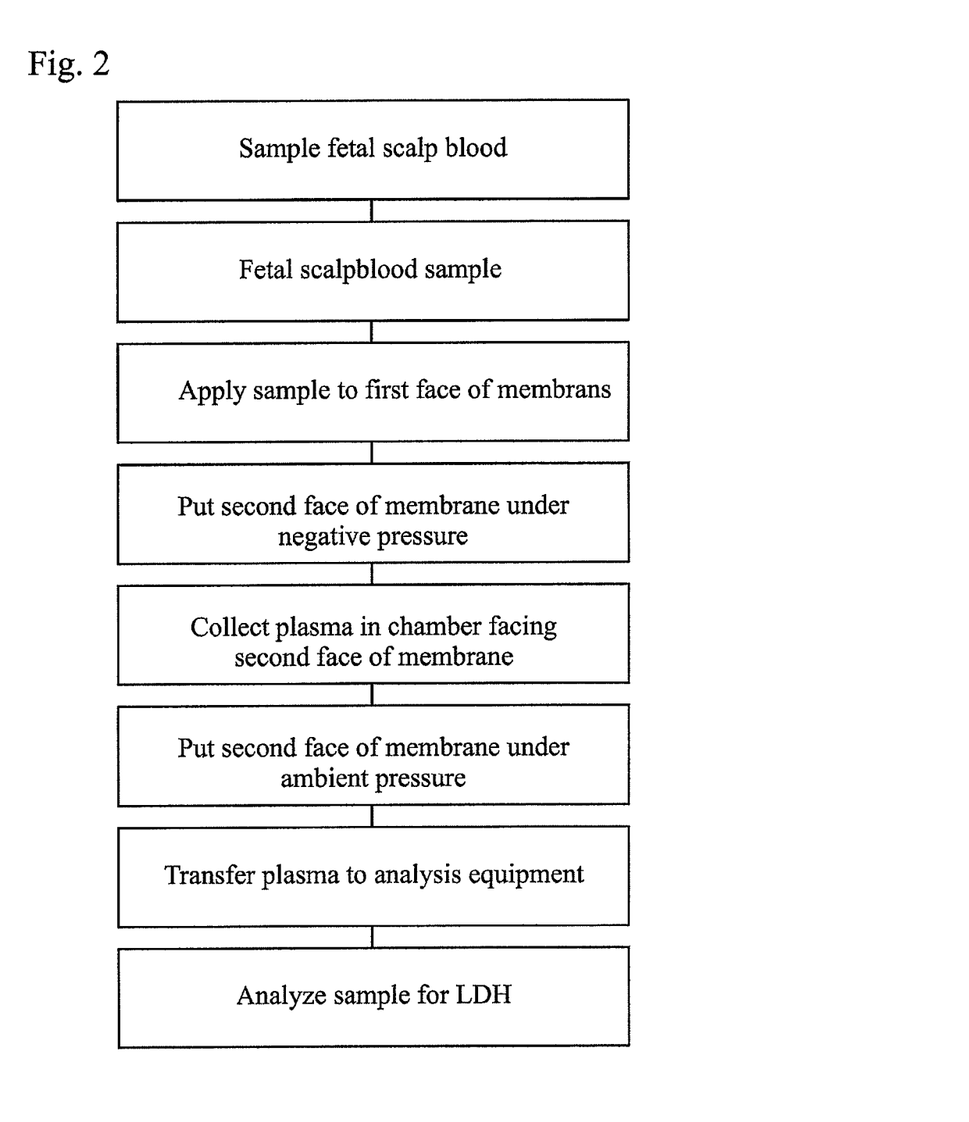
FIG. 2 depicts a block diagram schematically presenting an embodiment of the method of the invention.
Figure 3:
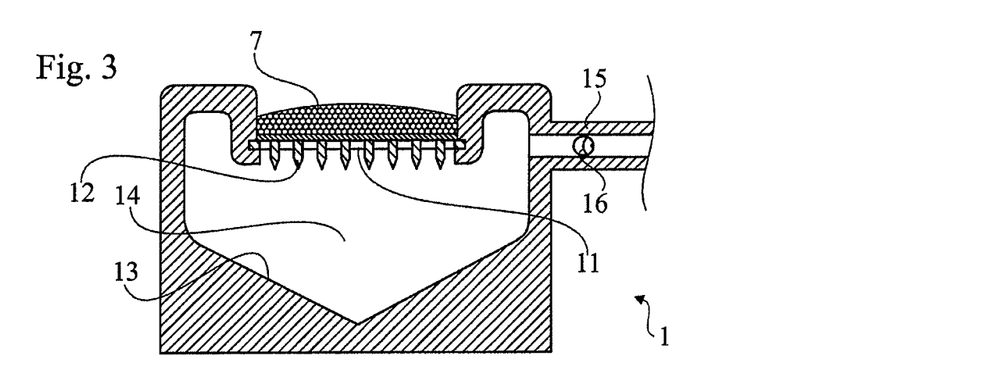
FIGS. 3-5 depict sectional views of a first embodiment of a separation device in consecutive stages of use in the method of the invention.
Figure 4:
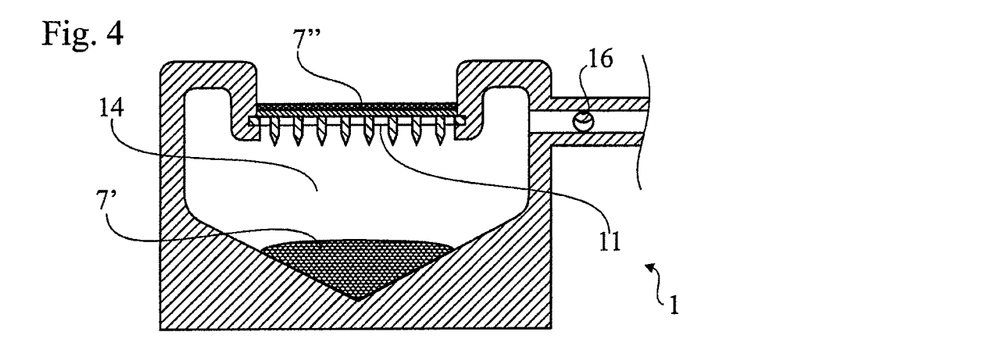
Figure 5:
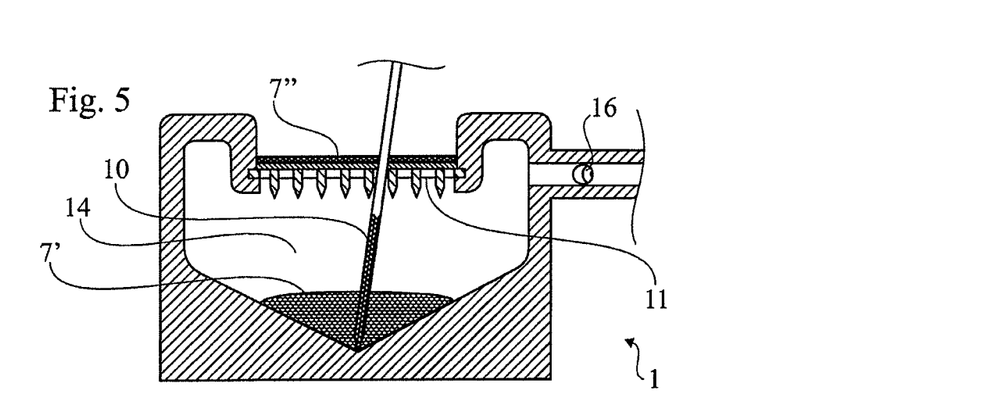

A plasma separation device 1 according to the invention is shown in FIGS. 3-5 in consecutive stages of use in the method. The device 1 comprises a generally circular housing in a hydrophobic polymer material such as poly(tetrafluoroethylene). A plasma collection compartment 2 in the housing has a top opening closed by a plasma separation membrane 11 supported by a grid 12 of same or similar material as that of the housing. The compartment bottom 13 slants towards its center in the form of a wide-angled cone. From a side wall of the compartment 14 extends a tubular conduit 15 provided with a valve 16. The conduit 15 extends to a source of negative pressure such as a vacuum pump (not shown). In FIG. 3 a 40 µL sample 7 of scalp blood has been deposited on the exterior face of the membrane 11, the valve 16 being in a closed position. By opening the valve 16 the compartment 14 is put under negative pressure (FIG. 4); thereby plasma 7' is sucked into the compartment 14 accumulating on its slanting bottom 13, the blood cells 7" being retained by the membrane 11. After closing the valve 16 the state shown in FIG. 5 is reached in which the pressure in the compartment is equalized with ambient pressure by air sucked through the membrane 11. Alternatively pressure equalization in the compartment 14 can be achieved through conduit 15 after stopping the generation of negative pressure, or in any other suitable way. FIG. 5 illustrates the removal of the plasma sample 7 from the compartment 14 by means of an aspirating syringe, the cannula 10 of which has been inserted through the membrane 11. To avoid contamination of the plasma sample 7 by blood cells on the membrane a separate insertion port (not shown) can be provided such as, for instance, a rubber septum disposed in a separate opening in a top or side wall of the device 1. The block diagram of FIG. 2 illustrates the principles of the method of the invention.

The compartment may additionally be provided with a second conduit arranged to communicate with a bottom section thereof provided with a second valve means for controlled emptying of fluid (plasma) accumulated at the bottom of the compartment. Alternatively, the compartment may comprise means for determining LDH and other markers in the accumulated plasma. It is preferred for the membrane to have an area of from 5 $mm^2$ to 1000 $mm^2$, in particular from 20 $mm^2$ to 300 $mm^2$.

Scalp blood analysis. The analysis was successfully repeated with scalp blood sampled from a healthy male adult with standard equipment used in clinical routine for pH or lactate measurement. Samples were with and without the use of a vaginal tube (to avoid contamination by amniotic fluid in a real life situation). The time from application of the blood sample to the plasma separation card to the display of the result was 7 minutes at average. It is obvious that the time for analysis can be considerably shortened, such as to three to four minutes and even less, by using equipment adapted to the method, in particular a separation card in which the negative pressure applied to vacuum side of the membrane is well controlled and timed, such as by the use of electronic means. Thus the use of the method of the invention in the determination of fetal scalp blood bedside in an emergency situation is perfectly feasible.

In the measurements it was found that LDH was substantially higher in scalp blood than in finger capillary blood; LDH: 1044 U/L and 1127 U/L in scalp blood with and without the use of an amniotic tube, respectively, vs. 400 U/L in finger blood. A divergence between scalp and cord blood similar to that seen for LDH in adult males has been observed in respect of glucose and haemoglobin concentration in fetus. It seems that the measurement of LDH in fetal scalp blood is unknown in the art.

Figure 6:
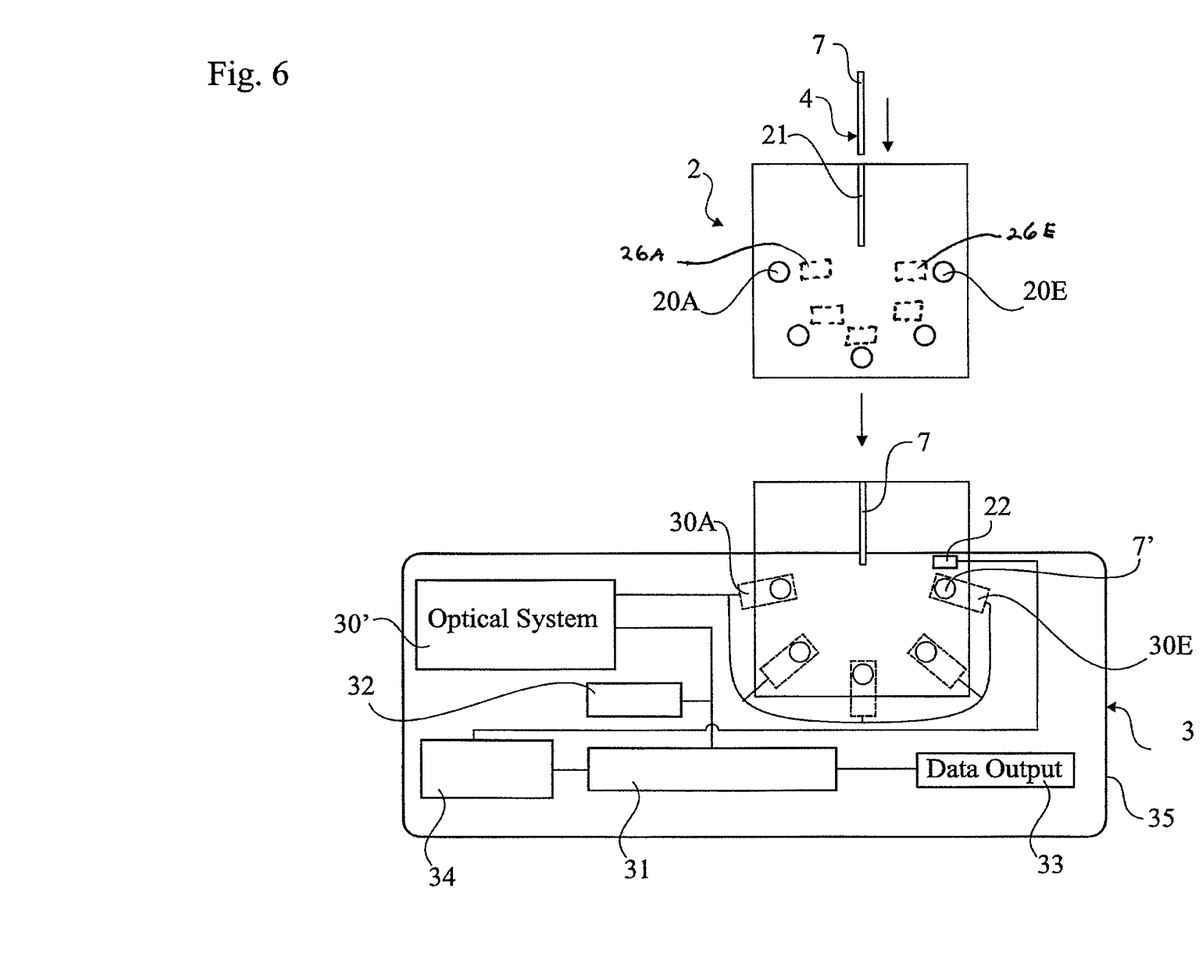
FIG. 6 presents an embodiment of capillary device according to the invention, intended to be used for collecting and testing scalp blood.

In FIG. 6 there is shown a system according to the invention including a disposable card 3 and an analyzing instrument 3 for performing point of care testing, i.e. in an environment nearby the patient, to allow for presenting a test result within 7 minutes, preferably within 2 minutes and more preferred within seconds. The disposable card 2 is preferably arranged with a number of different detection cells 20A-20E, as will be explained more in detail in connection with FIG. 7, but indeed a card merely testing LDH (or e.g. two cells for LDH+AST) may in some applications be sufficient.

In FIG. 6 two consecutive steps according to the method of the invention are presented. At the upper left-hand side there is shown the first step where new card 2 is provided to be supplied with test blood 7 by means of a glass capillary device 4, being filled with whole blood amounting to, e.g. about 10 µL. In a consecutive step the glass capillary device 4 has been inserted into a compartment 21 of the card 2 to interface the blood sample 7 with the card 2 and the disposable card 2 placed into the instrument 3, whereby a directly analysis of the blood sample 7 may be performed as will be explained more in detail in connection with FIG. 7. The card is provided with devices (as known per se, e.g. micro fluidic channels for distribution of plasma/serum) to allow for plasma 7' from the blood sample 7 to enter into at least one of the detection cell 20A-20E, and preferably blood cells in at least one other cell and more preferred hole blood to at least one other cell. Prior to entering the detection cells the plasma/serum/whole blood enter into a reaction chamber (26A-26E) where reagents (preferably dried) are deposited. Accordingly reaction will take place prior to the detection. In the instrument 3 there are positioned optical devices (as known per se, and for example described in U.S. Pat. No. 4,935,346 (which is hereby incorporated by reference) performing optical measurements. The optical measurement (e.g. spectrophotometry as known per se and described in U.S. Pat. No. 4,803,159 which is hereby incorporated by reference) will directly be handled by the processor 31 of the instrument 3 and shown in display 32 and/or provided as a data output 33, e.g. on a printed paper. Further the analyzing instrument 3 is preferably provided with bar code reading arrangement 34 enabling reading and processing a bar code 22 with a unique code for each disposable card 2. Preferably the analyzing instrument 3 is enclosed within a housing 35 to make it portable. Connections (not shown) are provided to supply the instrument 3 with necessary supplies, e.g. power (if not battery operated). In an alternative embodiment the instrument may be made smaller by using an external processor, e.g. of a laptop making the instrument connectable to laptop, e.g. by means of a USB cable.

Figure 7:
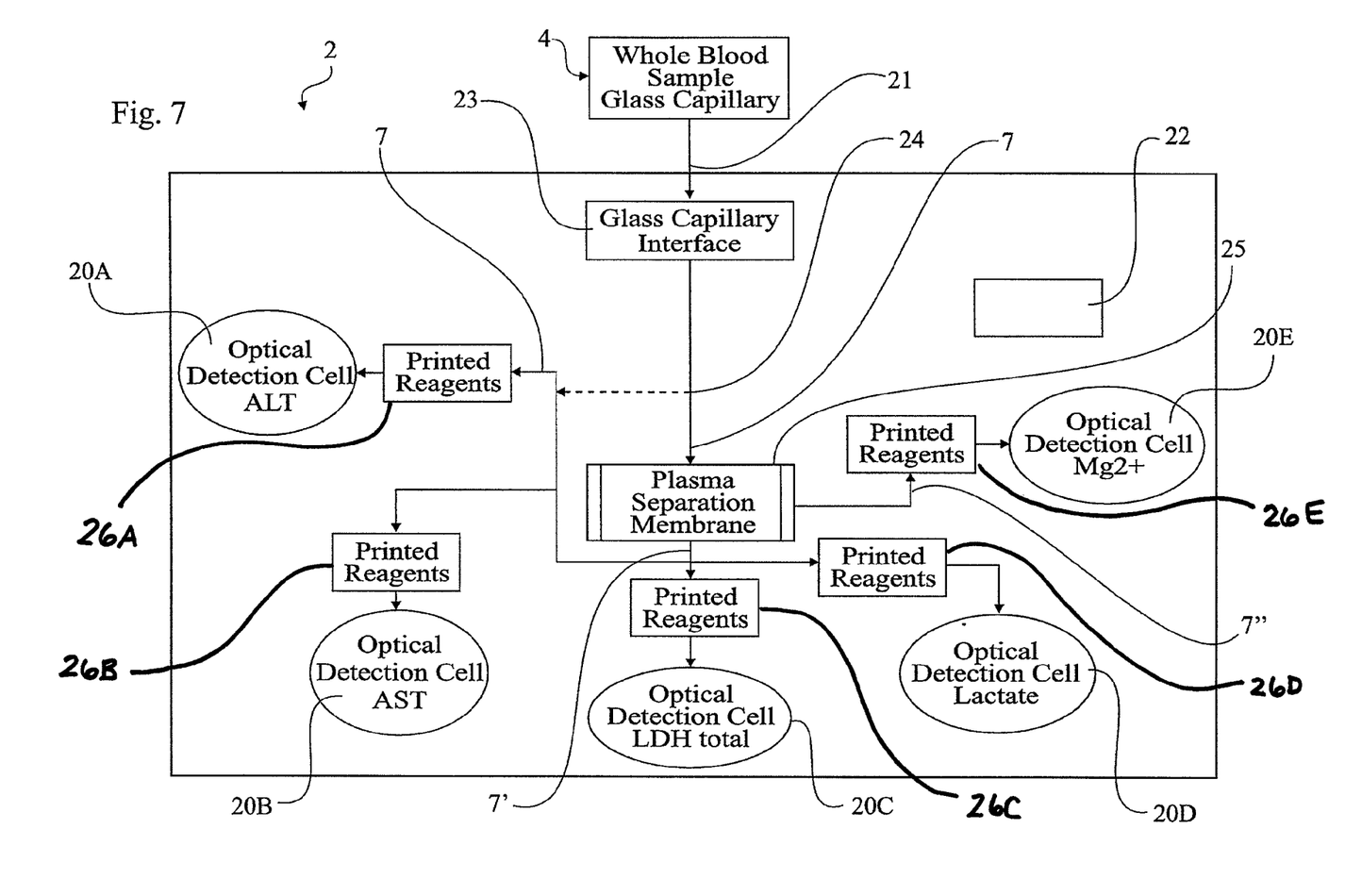
FIG. 7 presents a quick test analyzing system according to another embodiment of the invention.

In FIG. 7 there is shown an embodiment of an exemplary disposable card 2 according to the invention. The card 2 is arranged with five detection cells 20A-20E, all of them being optical detection cells. The first detection cell 20A is for ALT. The second detection cell 20B is for AST. The third detection cell 20C is for LDH total. The fourth and fifth detection cells 20D, 20E are for lactate and $Mg^{2+}$ respectively. The card according to the shown embodiment has a circular flat shaped body 23, having a diameter which makes it easy to handle, e.g. a diameter within the range of 20-120 mm, preferably 40-100 mm. The material of the body 23 may be chosen from a wide range, for example poly(tetrafluoro)ethylene, polyethylene, polypropylene, polystyrene and similar. As schematically presented in FIG. 7 the card 2 is provided with a chamber 21 adapted to be fitted with a glass capillary device 4 supplying a blood sample 7. In connection with the chamber 21, at the bottom thereof there is an interface 23, that in a manner known per se safeguards further transport of the blood sample, e.g. to the plasma separation device 25 (including a membrane and a plasma collection compartment, please compare with the membrane 11 shown in FIGS. 3-5). In between the plasma separation membrane 25 and the interface 23 there may optionally be provided a sample splitter 24 (as indicated by dotted lines) to provide the possibility to supply whole blood to some detection cells, e.g. via printed reagents 26A, B, to detect ALT and AST respectively. A larger amount of the sample of whole blood may then possibly be supplied to the plasma separation device 25, e.g. to via printed reagents 26C, D detect LDH total and lactate respectively in the plasma 7'. Blood cells 7" obtained after separation may be conducted after mixing with a printed reagent 26D to optical cell 20E to detect $Mg^{2+}$.

In the following test results will be described wherein different combinations of markers are being used in exemplary disposable cards according to the invention.

Lactate dehydrogenase is increasing during hypoxia and is present in all of the body's cells. LDH present in the blood stream indicates hypoxia severe enough to reduce the blood flow to peripheral organs. This is the onset on leakage of LDH from these cells. By detecting LDH it is not possible to determine which organ that is suffering from hypoxia. If haemolysis has occurred (rupture of red blood cells will also cause an increase in LDH, even if it is not by hypoxia). Haemolysis is divided into two groups: (1) In vitro, which means that the haemolysis occur when taking the sample or at storage in test tubes, and (2) In vivo which means that the red blood cells within the patient have ruptured due to illness. An ongoing haemolysis will then give falsely high levels of LDH, not due to only hypoxia. The half-life (T1/2) for LDH is dependent on which type of the five isomers of LDH that has leaked out into the blood. LDH1 which is mainly present in the heart, brain and red blood cells has T1/2 120 h while LDH5 mainly appears in the liver and muscles have T1/2 at 10 h.

|  |  | High LDH | | |
|---|---|---|---|---|
|  |  | No | Yes | Total |
| HIE | No | 178 | 6 | 184 |
|  | Yes | 0 | 10 | 10 |
| Total |  | 178 | 16 | 194 |

In our study in newborn infants all the patients with HIE would be found by using LDH as a marker as well as 178 of 184 healthy patients. This means that no case of hypoxia would be missed and 6 babies would be unnecessarily delivered by caesarean section or by instrumental delivery.

High LDH indicates ongoing or a recent episode of hypoxia somewhere in the body or haemolysis.

AST is an enzyme that is present in many of the organs in the body but is more organ specific than LDH. AST is mainly present in the liver, muscles and red blood cells. AST is, as well as LDH, sensitive towards haemolysis but not to the same extent.

T1/2 for AST is 12-15 h for newborns.

|  |  | High AST | | |
|---|---|---|---|---|
|  |  | No | Yes | Total |
| HIE | No | 210 | 26 | 236 |
|  | Yes | 0 | 12 | 12 |
| Total |  | 210 | 38 | 248 |

In our study all the patients with HIE would be found by using AST as a marker as well as 210 of 236 healthy patients. This means that no case of hypoxia would be missed and 26 babies would be unnecessarily delivered by caesarean section or instrumental delivery.

High level of AST indicates ongoing or a recent episode of hypoxia in the liver or muscles or haemolysis.

ALT is a specific enzyme for the liver and is very little affected by haemolysis.

T1/2 for ALT is 36 h.

|  |  | High ALT | | |
|---|---|---|---|---|
|  |  | No | Yes | Total |
| HIE | No | 212 | 28 | 240 |
|  | Yes | 0 | 12 | 12 |
| Total |  | 212 | 40 | 252 |

In our study no baby with brain damage would be missed if ALT is used as a single marker but 28 of 240 healthy patients would be unnecessarily delivered by caesarean section or instrumental delivery.

An elevated level of ALT indicates an ongoing or an episode of hypoxia in the liver.

The magnesium in the body is to 50% located in the skeleton and 50% inside cells. If an acidosis occurs (lowered pH), for example during hypoxia, hydrogen ions will move in to the cells. Mg will at the same time be transported out of the cells into the blood which leads to elevated Mg levels in the blood. For newborns with HIE the Mg levels are lower than for healthy newborns. Mg is more of a marker for acidosis than cell damage.

An elevated Mg level is an indication of acidosis which is a symptom for hypoxia. A low Mg level is an indication of an episode of hypoxia that led to brain damage.

At the present stage we have no data on Mg during labor. However; we rely on the increase in Mg levels that have been seen in our animal studies on newborn piglets.

The table below present results based on using LDH+AST as markers.

|     |     | highAST + LDH |     |      |       |
| --- | --- | --- | --- | --- | --- |
|     |     | No  | One | Both | Total |
| HIE | No  | 170 | 11  | 3    | 184   |
|     | Yes | 0   | 0   | 10   | 10    |
| Total |   | 170 | 11  | 13   | 194   |

The findings show that all healthy babies have low levels of AST and/or LDH. Out of the 10 babies with HIE all babies had both high levels of AST and LDH. Three babies with elevated AST and LDH levels did not suffer from HIE. AST adds on the effect of using LDH to determine when the baby is healthy.

High levels if LDH and AST indicate hypoxia and haemolysis.

The table below presents results based on using LDH+ALT as markers.

|     |     | highALT + LDH |     |      |       |
| --- | --- | --- | --- | --- | --- |
|     |     | No  | One | Both | Total |
| HIE | No  | 163 | 20  | 1    | 184   |
|     | Yes | 0   | 0   | 10   | 10    |
| Total |   | 163 | 20  | 11   | 194   |

The table above shows that if LDH and ALT are analyzed at the same time all healthy babies have low levels of ALT and/or LDH. Out of the 10 babies with HIE all babies had elevated levels of both ALT and LDH. One baby with elevated levels of AST and LDH did not suffer from HIE. ALT adds to the effect of using LDH to determine when the baby is healthy.

ALT is also of interest since it theoretically would be able to tell if the baby suffered from hypoxia earlier when still in uterus since ALT will remain in the blood for a long time (T1/2 is36 h).

Elevated levels of LDH and ALT indicate hypoxia that has affected the liver (amongst other organs).

The table below presents results based on using LDH+ALT+AST as markers.

|     |     | highALT + LDH + AST |     |     |     |       |
| --- | --- | --- | --- | --- | --- | --- |
|     |     | No  | One | Two | All | Total |
| HIE | No  | 158 | 20  | 5   | 1   | 184   |
|     | Yes | 0   | 0   | 0   | 10  | 10    |
| Total |   | 158 | 20  | 5   | 11  | 194   |

If LDH is analyzed together with both AST and ALT and all of the enzyme levels are low no baby with HIE can be found. At an elevation of all three markers all babies with HIE are found and only one baby is unnecessarily delivered without HIE.

High LDH+ALT+AST is indicating an ongoing hypoxia or hypoxia during the previous hours. The fact that the half-life of ALT is 24 h longer than AST and LDH makes this combination a possibility to also give a time aspect of the hypoxia. For example of LDH+ALT+AST are all high and still are increasing over the first 24 h after the birth of the baby that indicates hypoxia appeared in close proximity to the delivery.

In the material used for these calculations actually 23 caesarean sections and 22 instrumental deliveries were performed in the group that showed no indications on hypoxia (HIE, acidosis or low Apgar score). Here are only the caesarean sections performed due to suspected harm for the babies are included.

In the example above it is shown that by using LDH in combination with ALT only one baby is unnecessarily delivered instead of 45. This gives a saving of 880 000 SEK only in the cost for caesarean sections, the cost for vacuum extraction not included. Vacuum extraction is increasing the risk for injuries for both the mother and the baby which generates cost for the healthcare in combination with increased suffer for the patient.

As seen above AST is not adding much to the method when it comes to determine weather the baby suffers from hypoxia or not. AST is still adding information due to the half-time of 12 h. Together with ALT and repeatedly taking samples after birth these two enzymes are able to give information on when hypoxia occurred. This is of great juridical value since obstetricians today have problems to prove if the missed a case of hypoxia or if the baby already suffered from hypoxia when the woman arrived the hospital for labor.

A conclusion based on information from scientific literature indicates that magnesium would add to the knowledge about whether the hypoxia is present or was a previous episode.

High levels of LDH+ALT+AST +Mg indicates an ongoing hypoxia severe enough to affect peripheral organs and give acidosis. High levels of LDH+ALT+AST but low Mg indicates a recent episode of hypoxia that gave rise to organ damage and also probably affected the brain. Mg is not sensitive towards haemolysis and together with ALT it strengthens that the elevated levels of LDH are due to organ damage and not haemolysis.

In the following an example will be described in actual use of the method and devices respectively according to the invention, assuming that a patient named Anna arrives to a delivery room to give labor. The personnel starts with controlling the baby's condition by examining the heart frequency with a small piece of equipment on the woman's stomach (fetal heart rate pattern, CTG). At intervals controls with the CTG are performed to observe possible changes. After eight hours of labor and Anna is opened 8 cm. At a new CTG control it shows that the heart rate of the child is elevated. The midwife calls on the obstetrician on call who wants to continue to take a sample from the baby's scalp to see if there are any other signs on illness.

Anna, who was lying on her side, is asked to move into gynelogical position and the obstetrician puts a metallic tube through the vagina and pushes it to the scalp of the baby. She washes away amniotic fluid and makes a small cut in the baby's scalp (scalp sample). When she sees a drop of blood 7 she takes a capillary tube 4 and takes about 10 μl of blood. (It is not easy to get blood through the small tube at the same time as you need it to be clean and work fast. 30-40 μl is quite a large volume in this setting and that is what is needed for scalp samples detecting pH.)

The midwife is next to the obstetrician providing a disposable card 2 where the doctor is inserting the capillary tube 4.

The card 2 with the blood 7 is then inserted into a detection instrument 3 positioned nearby where levels of LDH, AST, ALT and magnesium are analyzed by a spectrophotometer 4. The analyses takes place after the separation of red blood cells 7″ on the card 2 and the remaining plasma 7′ reacts with reagents 20A-D on the card. Within minutes (e.g. about two minutes) the result shows on a display on the instrument. It shows "normal-normal-normal-normal" which tells the obstetrician that none of the markers LDH, AST, ALT and magnesium are at elevated levels. Anna is continuing the labor by natural means and is later giving birth to a healthy child.

Later the same night the obstetrician is called into room 3 where Helena is giving birth to her first child. Here as well the CTG is not satisfactory and a scalp sample is taken. This time the display shows "high-high-high-high" which tells the obstetrician that all of the markers are at elevated levels. This can only mean that the baby suffers from an ongoing hypoxia and a decision to make an emergency caesarean section is made. An alarm to the surgery is made and Helena is rushed to the room still in her bed. A fast anaesthetic is done while the obstetrician washes her hands and changes to surgical clothes. She is then doing a cut in the skin and the uterus and a baby is delivered only minutes after the alarm.

As described above some of the markers are sensitive towards haemolysis. The influence of heamolysis on the method is not fully investigated at the present stage, but it seems that it will not drastically change the outcome in at least some situations. However, if it will show that haemolysis is appearing frequently during sampling it is foresome to integrate a marker for haemolysis in the card. The most probable scenario is that we will use free haemoglobin (Hb) as the marker of choice. By measuring Hb in plasma information about haemolysis has occurred and if it has it will also be possible to see how severe. It is also possible to take that into account and recalculate the enzyme levels depending on the degree of haemolysis.

In some situations LDH alone or LDH in combination with for example lactate, ALT, AST, or magnesium, may be enough to judge how the baby is doing, if so the analysis can be calorimetric (change of colour of the reagents).

Figure 8:
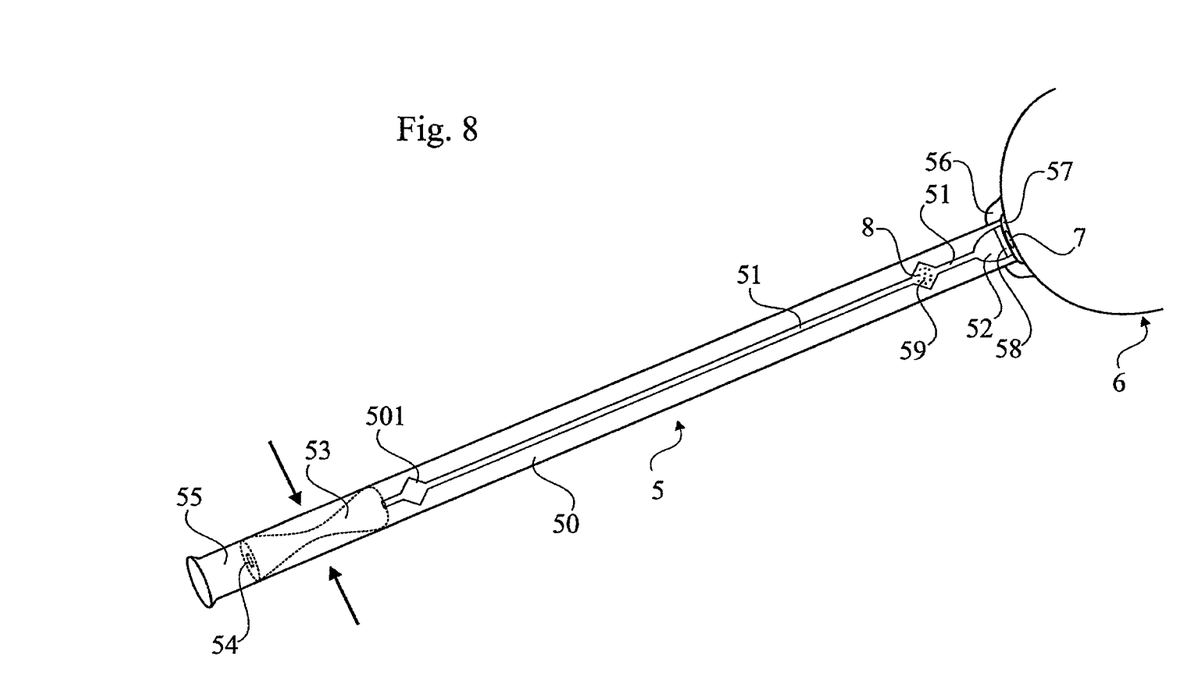
FIG. 8 presents an embodiment of disposable card device for a quick test according to the invention.

In FIG. 8 there is shown an embodiment of alternative testing arrangement, wherein dry chemistry is used to perform the analysis. An advantage with testing device 5 as shown in FIG. 8 is that no power supply at all would be needed. The testing device 5 is arranged with elongated tube formed body/casing 50. Within the elongated body 50 there is a channel 51 opening up into a front chamber 52 positioned adjacent the front end of the housing 50. At the other end of the channel 51 there is, near the rear end of the housing 50, there is provided a pumping device 53. The pumping device 53 is in the form of a resilient hollow body arranged with a check valve 54 at the outlet end thereof. The outlet (via the check valve 54) opens up into a disposal compartment 55. At the front end of the housing 50 there is arranged a collar device 56 having a centrally positioned hole 57 communicating with the front chamber 52 via a filter 58, that filters out blood cells. At a distance from the front end, forming part of the channel 51, there is a further chamber 59 arranged with dry chemistry means 8. Also as a part of the channel 51 adjacent the pumping device 53 there is arranged a further chamber 501 creating a buffer and also providing indication regarding volume of blood 7 in the channel 51.

The testing device shown in FIG. 8 is intended for use in connection with labor. As schematically presented in FIG. 8 scalp of the head 6 of a child is penetrated to obtain a drop of blood 7 (as in known per se). Thereafter the testing device 5 is introduced via the vagina and put onto the blood sample 7, by positioning the collar 56 around the blood drop 7. In a next step the pumping mechanism 53 is activated wherein the check valve 54 will open up to let air escape from the hollow inner of the resilient pumping device 53. When the pumping device 53 is released a vacuum will be created (thanks to the resiliency), which is communicated to the blood drop 7 via the channel 51, whereby blood will be sucked into the channel 51 via the filter 58. Accordingly blood plasma 7′ will enter into the analyzing chamber 59. The pumping mechanism may be applied a number of times to safeguard sufficient blood for the testing, which may be determined once blood is observed in the buffer chamber 501. Thereafter the testing device 5 is removed and by observing the colour of the chemical means in the analyzing chamber 59 it may be determined if the child is suffering from hypoxia. As is known per se the dry chemical means 8 may be used to indicate different measures to be taken depending on which colour is presented. For instance the following colours could be used to indicate which measure is to be taken. If it shows a green colour no measure should be taken. If a red colour is presented the child should be taken out as quickly as possible. If yellow colour is presented a new sample should be taken within less than 20 minutes.

Clinically the testing device 5 would give the same kind of indications as above. It is evident that the use of a capillary tube to collect the blood from the baby's scalp, could also be combined with a slightly modified testing device 5, but preferably also designed such that when the blood is collected a closed system is created within the device 5. This can be achieved in many ways, e.g. by pushing the top with a silicon collar (as shown) against the scalp of the baby or by removing the device 5 and attach a tight sealed cap on the top (not shown).

We also foresee that the lactate test that is used today can be analyzed in combination with the method of the invention.

Figure 9:
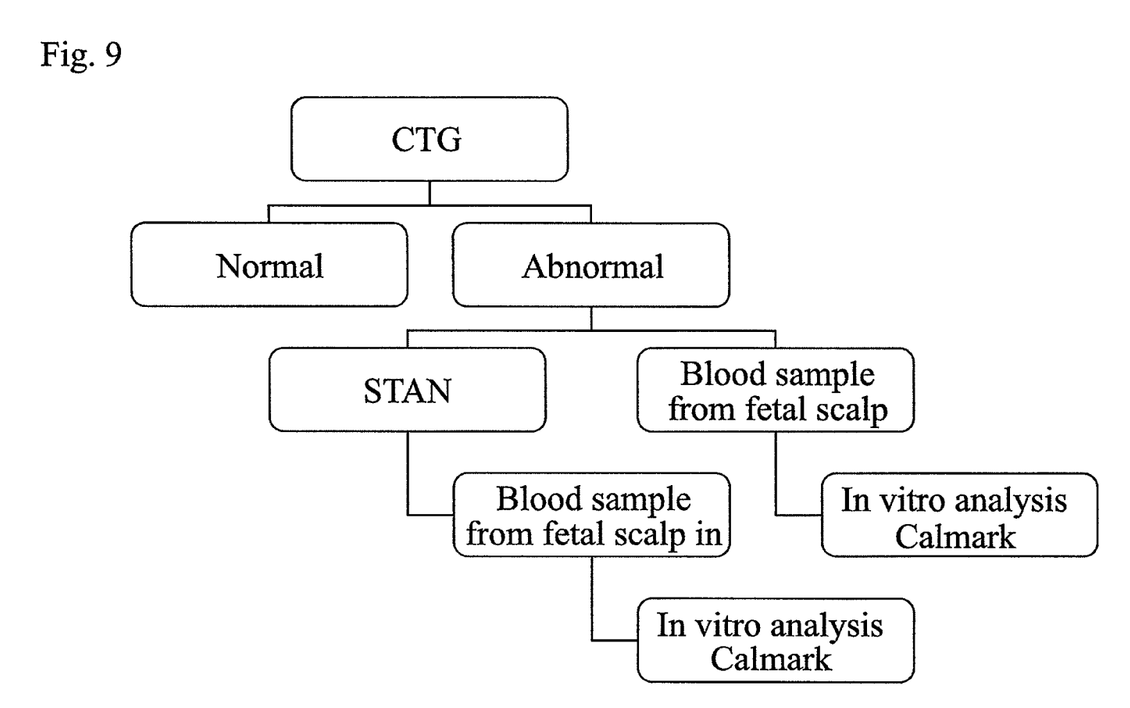
FIG. 9 presents a diagram of actions taken normally in conjunction with the invention.

In FIG. 9 there is shown a flow chart on when to preferably use the method and devices respectively according to the invention. As is presented in the flow chart CTG should preferably be used as a primary indicator. If the CTG is normal no measure would normally be necessary to undertake. However if the CTG is abnormal either directly a blood sample from the child's scalp should be analysed according to the invention or possibly it may be proceeded by a ST-analysis of the fetal heart.

The invention is not limited by what has been described above but may be varied within the scope of the appending claims. For instance it is evident for the skilled person that the definition "scalp blood" also blood samples collected from other parts of the body may at occasions function to obtain the advantages according to the invention. Samples to be used with the invention include whole blood, blood plasma and blood serum.

In another aspect, embodiments of the invention can be beneficially used in other medical circumstances. In one embodiment, a blood sample is collected from a location of interest prior to a medical procedure and analyzed for prognostic markers. Preferably, the plasma and blood cells are separated from each other prior to determining the respective amounts of prognostic markers in the plasma (e.g., total amount of LDH in the plasma). After the medical procedure has been completed, a second blood sample can be obtained from the point of interest and analyzed in the same manner as the initial sample. The determination of prognostic markers in each sample can determined and compared to assess the presence of hypoxia.

In various embodiments, multiple prognostic markers are analyzed. Such embodiments comprise determining total amount of LDH and at least one additional prognostic marker in the plasma of both blood samples selected from the group consisting essentially of K, Mg, Ca, AST, ALT and lactate. Accordingly, the respective amounts of each prognostic marker in the first and second samples can be compared to identify a proper location for an anastomosis. In one embodiment, the medical procedure comprises anastomosis of the gastrointestinal tract.

For example, colorectal cancer is one of the most common tumors in both genders. The current treatment involves a surgical procedure where the tumor is removed together with a radical part of the bowel. In the majority of these cases the distal and the proximal ends of the bowel are thereafter put together again. This is referred to as an anastomosis.

As such, certain embodiments comprise a method of determining hypoxia from a blood sample collected from a mammal's gastrointestinal tract (e.g. bowel). As such, certain embodiments comprise a point-of-care (POC) method for a quick (e.g. within minutes or seconds as discussed above) determination of hypoxia-ischemia from a small blood volume. Thus, these embodiments can make it possible to decide if the chosen part of the bowel is suitable for anastomosis or not.

LDH, AST, magnesium and lactate are markers that increase in blood due to cellular damage and anaerobic metabolism during hypoxia-ischemia. Before the vessels are extirpated, blood from the bowel can be collected using a scalpel (or the like) and a sterile capillary. The capillary can be inserted into an analysis card described above and analyzed. The result can preferably used as a unique patient reference value (e.g., a baseline). After a tumor (and the surrounding bowel) have been removed, a new test can be performed to see if the markers have increased. If so, the area for anastomosis can be relocated closer to the still existing blood supply to minimize the risk for hypoxia-ischemia induced anastomosis insufficiency and leakage.

In addition to sampling blood from the gastrointestinal tract, embodiments of the present invention can beneficially comprise collecting blood samples from a specific organ of interest or cerebrospinal fluid of a mammal during a surgical procedure.

For instance, the main reasons for surgery in the thoracoabdominal aorta are aneurysms and dissection. The extensive operation required is associated with significant morbidity and mortality. Some of the most common complications are neurological injuries. The reason for the majority of these complications is insufficient oxygen and energy supply due to ischemia. As an example, such operations cause permanent paralysis as a post operative complication in 1-10% of the patients depending on the location for surgery on the aorta.

However, embodiments of the present invention comprise a method, which can be a POC method, for hypoxia-ischemia detection during surgery in blood from specific organs or cerebrospinal fluid (CSF) through a lumbar drain. As such, a sample from a specific organ of interest is obtained and analyzed for LDH as described in detail above. In a preferred embodiment, the method for detecting hypoxia includes determining LDH and at least one additional prognostic in the sample selected from the group consisting essentially of K, Mg, Ca, AST, ALT and lactate. Preferably, one of the additional prognostic markers determined includes lactate. By way of example, a specific organ of interest can include a mammal's aorta.

In another aspect, embodiments of the invention can improve the morbidity and mortality rates in patients after transplantation therapy. One of the key factors impacting morbidity and mortality rates in patients after transplantation is related to preservation injury of grafts, such as the hepatic grafts in a liver transplant. For example, LDH, AST and ALT leakage into the perfusate is an indication of loss of the membrane integrity of the liver cells.

In one such embodiment, the method for determining the presence of hypoxia in an organ to be transplanted into a mammal in need thereof can comprise collecting a blood sample and analyzing the sample, as described above, for prognostic markers prior to the transplantation surgery. In one embodiment, the sample is analyzed to determing the total amount of LDH and at least one additional prognostic marker in the sample selected from the group consisting essentially of K, Mg, Ca, AST, ALT and lactate. In one preferred embodiment, the organ for transplant comprises a liver.

Certain embodiments of the present invention can satisfy a need at clinics for identify patients with a risk of developing the critical condition multi organ dysfunction. Currently, some countries have developed a team of individuals consisting of physicians and nurses from the intensive care unit (ICU) for the purpose of providing a mobile team that could come to a medical, not intensive care, ward for assessment of a patient at risk of multi organ dysfunction. If identified as being at risk, a patient can be treated and transferred to the ICU. In Australia the introduction of these mobile teams has reduced the incidence of cardiac arrest, sudden death due to cardiac arrest, post operative complications and days at ICU by as much as 50%.

These mobile teams perform a clinical examination of the lungs, kidneys and circulation to assess the risk of multi organ dysfunction. However, there is no quick reliable method for assessment of the liver or metabolism. The liver is frequently affected by severe disease and liver enzymes and metabolic acidosis is predictive of mortality.

Accordingly, devices according to embodiments of the present invention are well suited for use by such teams. Such devices are typically small and quick enough for a mobile team to bring (e.g in a bag) when consulting on a ward. Since LDH, AST and ALT are present in liver cells and lactate is elevated during metabolic acidosis, these teams can now add the assessment of the liver to the other parameters examined by utilizing a device according to the present invention. Thus, devices and methods according to embodiments of the present invention can potentiality identify even more patients in risk of severe illness and therefore save both humanitarian and economical costs.

In another aspect, devices and methods according to certain embodiments are well suited for use by staff in the intensive care unit (ICU). The ICU is responsible for the most critically ill patients in the health care system. Independently, if the patient is taken to the ICU because of trauma, cardiac diagnosis, sepsis, haemorrhage or extensive surgery there is always a substantial risk of hypoxia if the circulation and saturation are insufficient. Even if the typical parameters are carefully monitored and abnormalities treated with fluids and drugs, there remains no bedside method capable of providing the ICU staff information about the effects of a treatment in the peripheral tissue.

It is known that a substantial increase in serum LDH, AST, ALT and lactate in patient with severe shock is an indicator of a bad outcome (e.g., death) (Hardaway 1981). AST, ALT (and previously also LDH) are measured as a clinical routine in many ICUs as a marker of hepatic damage and lactate is used as a marker of anaerobic metabolism and intestinal ischemia (Juel 2007). However, there remains no device that can be operated bedside or provide results in a matter of minutes.

Embodiments of the present invention include a device and a method for determining hypoxia bedside, wherein the results are available within a matter of a few minutes at most. Such embodiments include obtaining a sample for analysis and determination of LDH. In preferred embodiments, the methods include determining the amount of at least one additional prognostic marker in the plasma selected from the group consisting essentially of AST, ALT and lactate.

As discussed above, Acute perinatal asphyxia, that is, hypoxia (insufficient oxygen saturation of fetal blood) during or close to birth, remains an important cause of neurological damage in form of hypoxic-ischemic encephalopathy (HIE) in newborn infants. The pathological mechanism of hypoxia-ischemia leading to injuries of the neurons in the brain is biphasic starting with the primary phase directly after birth. If the infant is successfully resuscitated this primary phase will be followed by a free interval that continues for hours. In two out of seven asphyxiated infants this free interval will be followed by a secondary energy depletion resulting in delayed cell death in the child's brain and a clinical picture with seizures (also known as HIE). The free interval offers a possibility to minimize the delayed cell death by hypothermia treatment (cooling the child's brain to 34.5° C.). However, there is need for a method to predict if a child will develop HIE and therefore have benefits from hypothermia treatment and who will not.

Since it is of importance to start the hypothermia treatment as soon as possible after birth (the neuroprotective effects are best decreased 5.5 h after the asphyxia), a quick point of care system for detection of prognostic markers is of clinical value. Data has been collected from newborn infants showing that by determining the amount of LDH together with ALT offers a 100% sensitivity for prediction of HIE with a >96% specificity.

Certain embodiments of the present invention provide a diagnostic tool for the physician in the clinical workplace and in research around hypothermia treatment in neonates subjected to perinatal asphyxia. Further, embodiments of the present invention include a method for the determination of hypoxia, in which an individual is capable of predicting brain injury after prenatal asphyxia. Such methods include obtaining a sample for analysis of LDH as discussed in detail above. In preferred embodiments, the relative amounts of multiple prognostic markers can be determined. Preferably, the blood sample is treated such that the plasma is separated from the blood cells and the determination of the levels of the various prognostic markers is based on an analysis of the plasma alone. In another preferred embodiment, the method comprises determining the amount of LDH and at least one additional prognostic marker in the plasma selected from the group consisting essentially of AST, ALT and lactate. Most preferably, the amount of ALT is one of the prognostic markers determined.

In one method according to embodiments of the present invention, the method includes providing hypothermia treatment to a mammal in need thereof, wherein the determination of LDH (alone or with other prognostic markers) in the plasma indicate delayed cell death in a mammal's brain.

In yet another aspect, embodiments of the present invention can by used to assess the status of a mammal's limbs before, during, and after medical or surgical treatment. For instance, trauma, fractures and vessel occlusions can affect the circulation to peripheral limbs and muscles (e.g compartment syndrome). There exists a significant correlation between oxygen in ischemic muscle and levels of lactate and LDH is observed (Yamamoto 1988) and lactate is elevated in femoral blood in patients with peripheral arterial occlusive disease compared to control values (Rexroth 1988). Devices according to embodiments of the present invention make it possible to use enzyme and lactate levels to diagnose ischemia of a specific limb and also to assess the effects of most treatments.

Additionally, embodiments of the present invention comprise a method for determining hypoxia-ischemic by analyzing a sample from a limb of interest and determining the total amount of LDH in the plasma. Additional prognostic markers can be quantified at the same time as the determination of LDH. This allows an assessment of blood circulation to a mammal's limbs before, during, and after a medical or surgical treatment.

The skilled person realizes that a large variety of modifications may be performed without the use of inventive skill, departing from the description above, e.g. the use of glass or some other suitable material in place of plastic etc.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of assessing hypoxia in a gastrointestinal tract of a mammal, comprising:
   a. collecting a blood sample from the gastrointestinal tract, said blood sample comprising plasma and blood cells;
   b. separating the plasma from the blood cells;
   c. determining the amount of lactate dehydrogenase (LDH) in the plasma and comparing the amount of lactate dehydrogenase with lactate dehydrogenase in a control sample;
   d. assessing the presence of hypoxia at the gastrointestinal tract from the amount of LDH in the plasma; and
   e. identifying a location of anastomosis based on the assessment of hypoxia at the gastrointestinal tract.

2. The method of claim 1, further comprising determining the amount of at least one additional prognostic marker in the plasma selected from the group consisting essentially of K, Mg, Ca, aspartate aminotransferase (AST), alanine aminotransferase (ALT) and lactate.

3. The method of claim 1, wherein the volume of the blood sample comprises from 5 µL to 150 µL.

4. The method of claim 1, wherein the volume of the blood sample comprises from 5 µL to 25 µL.

5. The method of claim 1, wherein the volume of the blood sample comprises from about 5 to 15 µL.

6. The method of claim 1, wherein the plasma is separated from the blood cells by means of a semi-permeable membrane such that the plasma passes through the membrane and the blood cells are retained on the membrane.

7. The method of claim 1, wherein the blood sample is collected from a mammal's colorectal.

8. The method of claim 7, wherein the blood sample is collected prior to a medical procedure and further comprising:
   a. collecting a second blood sample after a medical procedure, said blood sample comprising plasma and blood cells;
   b. separating the plasma from the blood cells of the second blood sample; and c. determining the total amount of LDH in the plasma of the second blood sample.

9. The method of claim 8, wherein the medical procedure comprises anastomosis of the gastrointestinal tract.

10. A method of assessing hypoxia at a tissue site of a mammal, comprising:
   a. collecting a blood sample from the tissue site, said blood sample comprising plasma and blood cells;
   b. separating the plasma from the blood cells;
   c. determining the amount of LDH in the plasma and comparing the amount of lactate dehydrogenase with lactate dehydrogenase in a control sample; and
   d. assessing the presence of hypoxia at the tissue site from the amount of LDH in the plasma, and wherein the blood sample is collected prior to a medical procedure and further comprising:
   e. collecting a second blood sample after a medical procedure, said blood sample comprising plasma and blood cells;
   f. separating the plasma from the blood cells of the second blood sample; and
   g. determining the total amount of LDH in the plasma of the second blood sample and further comprising determining the amount of at least one additional prognostic marker in the plasma of both blood samples selected from the group consisting essentially of K, Mg, Ca, AST, ALT and lactate; and
   performing a medical procedure on the mammal based on the assessment of the presence of hypoxia at the tissue site.

11. The method of claim 10, further comprising comparing the amount of the prognostic markers in the blood samples.

12. The method of claim 10, further comprising determining the amount of at least one additional prognostic marker in the plasma selected from the group consisting essentially of K, Mg, Ca, AST, ALT and lactate.

13. The method of claim 12, further comprising determining the amount of ALT in the plasma.

14. A method of performing an anastomosis procedure on a patient in need thereof;
   collecting a first blood sample from tissue in a portion of a gastrointestinal tract in patient, said blood sample comprising plasma and blood cells;
   determining a reference value for the amount of lactate dehydrogenase (LDH) in the plasma from said first blood sample for said tissue;
   removing a portion of the patient's gastrointestinal tract;
   collecting a second blood sample from tissue in the gastrointestinal tract of the patient, said second blood sample comprising plasma and blood cells;
   analyzing the amount of LDH in plasma of the second blood sample to determine the amount of LDH in the plasma from said second blood sample; and
   comparing the reference value to the amount of LDH in plasma of the second blood sample, and selecting a location for anastomosis based on the comparison of the reference value to the amount of LDH in plasma of the second blood sample.

15. The method of claim 14, wherein the step of removing a portion of the patient's gastrointestinal tract also includes the step of removing a tumor.

16. The method of claim 14, further comprising deteimining the amount of at least one additional prognostic marker in the plasma selected from the group consisting essentially of K, Mg, Ca, aspartate aminotransferase (AST), alanine aminotransferase (ALT) and lactate.

17. The method of claim 14, wherein the volume of the blood sample for each of the first and second blood samples comprises from about 5 µL to 150 µL.

18. The method of claim 14, wherein the volume of the blood sample for each of the first and second blood samples comprises from about 5 µL to 25 µL.

19. The method of claim 14, wherein the volume of the blood sample for each of the first and second blood samples comprises from about 5 to 15 µL.

20. The method of claim 14, wherein the plasma is separated from the blood cells by means of a semi-permeable membrane such that the plasma passes through the membrane and the blood cells are retained on the membrane.

\* \* \* \* \*

UNITED STATES PATENT AND TRADEMARK OFFICE
CERTIFICATE OF CORRECTION

| | | |
|---|---|---|
| PATENT NO. | : 8,945,824 B2 | Page 1 of 1 |
| APPLICATION NO. | : 12/101470 | |
| DATED | : February 3, 2015 | |
| INVENTOR(S) | : Karlsson et al. | |

It is certified that error appears in the above-identified patent and that said Letters Patent is hereby corrected as shown below:

In the claims:

Column 20,
Lines 22 and 23, "deteimining the amount" should read --determining the amount--.

Signed and Sealed this
Twenty-fifth Day of August, 2015

Michelle K. Lee
*Director of the United States Patent and Trademark Office*